United States Patent
Zingaro (10) Patent No.: US 8,222,440 B2
(45) Date of Patent: Jul. 17, 2012

(54) COMPOUNDS AND METHODS FOR THE TREATMENT OF CANCER

(75) Inventor: Ralph A. Zingaro, College Station, TX (US)

(73) Assignee: The Texas A&M University System, College Station, TX (US)

( * ) Notice: Subject to any disclaimer, the term of this patent is extended or adjusted under 35 U.S.C. 154(b) by 829 days.

(21) Appl. No.: 12/087,682

(22) PCT Filed: Jan. 16, 2007

(86) PCT No.: PCT/US2007/001127
§ 371 (c)(1),
(2), (4) Date: Oct. 20, 2008

(87) PCT Pub. No.: WO2007/082104
PCT Pub. Date: Jul. 19, 2007

(65) Prior Publication Data
US 2009/0233894 A1  Sep. 17, 2009

Related U.S. Application Data

(60) Provisional application No. 60/759,218, filed on Jan. 13, 2006, provisional application No. 60/763,008, filed on Jan. 26, 2006.

(51) Int. Cl.
*C07F 9/00* (2006.01)
*A01N 55/02* (2006.01)
*A61K 31/285* (2006.01)

(52) U.S. Cl. .............................. 556/71; 556/76; 514/504

(58) Field of Classification Search .................... 556/76, 556/71; 423/60; 487/27; 546/3; 514/504, 514/188
See application file for complete search history.

(56) References Cited

U.S. PATENT DOCUMENTS

| 6,911,471 B2 * | 6/2005 | Zingaro et al. ................ 514/504 |
| 6,995,188 B2 * | 2/2006 | Zingaro et al. ................ 514/504 |
| 7,405,314 B2 * | 7/2008 | Zingaro et al. .................. 556/71 |
| 7,619,000 B2 * | 11/2009 | Zingaro et al. ................ 514/504 |
| 2005/0131062 A1 | 6/2005 | Zingaro et al. |
| 2008/0090793 A1 * | 4/2008 | Zingaro et al. ................ 514/188 |
| 2008/0090904 A1 * | 4/2008 | Zingaro et al. ................ 514/504 |

FOREIGN PATENT DOCUMENTS

| WO | WO-03/057012 A | 7/2003 |
| WO | WO-2006/020048 A2 | 2/2006 |

OTHER PUBLICATIONS

International Search Report for PCT/US2007/001127 dated Aug. 27, 2007.
Daniel, James R. et al., "6-Thio-and-seleno-D-galactose esters of dimethylarsinous acid," Carbohydrate Research, 64:69-79 (1978).

* cited by examiner

*Primary Examiner* — Sreeni Padmanabhan
*Assistant Examiner* — Kendra D Carter
(74) *Attorney, Agent, or Firm* — Wilmer Cutler Pickering Hale and Dorr LLP (57) ABSTRACT

The present invention provides organic arsenicals which may be used to treat numerous human tumor cell lines, both of solid and hematological origin, as well as against malignant blood cells from patients with leukemia.

11 Claims, 2 Drawing Sheets

COMPOUNDS AND METHODS FOR THE TREATMENT OF CANCER

RELATED APPLICATIONS

This application is a national stage filing under 35 U.S.C. 371 of International Application PCT/US2007/001127, filed Jan. 16, 2007, which claims the benefit of U.S. Provisional Application Nos. 60/759,218, filed Jan. 13, 2006, and 60/763,008, filed Jan. 26, 2006, the contents of which are incorporated herein by reference in their entirety. International Application PCT/US2007/001127 was published under PCT Article 21(2) in English.

FIELD OF THE INVENTION

The present invention relates generally to the field of anti-cancer therapy. More particularly, it provides organic arsenic compounds and methods for their use in treating cancers such as leukemia and solid tumors.

BACKGROUND OF THE INVENTION

Despite progress in leukemia therapy, most adult patients with leukemia still die from disease progression. Arsenic trioxide, an inorganic compound, has been approved for the treatment of patients with relapsed or refractory acute promyelocytic leukemia (APL) and is being evaluated as therapy for other leukemia types. Preliminary data from China and the recent experience in the U.S., however, suggest a role for arsenic trioxide in the other hematologic cancers as well. Consequently, the activity of arsenic trioxide as an anti-leukemic agent is currently being investigated in many types of leukemia. Although the results look favorable in terms of the response rate of some of the leukemia types that are being investigated, systemic toxicity of arsenic trioxide is a problem (Soignet et al., 1999; Wiernik et al., 1999; Geissler et al., 1999; Rousselot et al., 1999).

The only organic arsenical (OA) manufactured for human use, melarsoprol, has been evaluated for antileukemic activity (WO9924029, EP 1002537). Unfortunately, this compound is excessively toxic to patients with leukemia at concentrations used for the treatment of trypanosomiasis. Therefore, there is a need to identify arsenic derivatives that can be used for the treatment of hematologic malignancies and cancer in general, that have similar or greater activity and lower toxicity than arsenic trioxide.

SUMMARY OF THE INVENTION

One aspect of the present invention provides organic arsenical compounds with anti-cancer properties. In some embodiments, the present invention provides compounds having a structure of formula (I) or a pharmaceutically acceptable salt thereof (I)

wherein
X is S or Se;

W is O, S, or (R)(R), where each occurrence of R is independently H or $C_{1-2}$alkyl;
n is an integer from 2 to 20, preferably from 5 to 20;
$R^1$ and $R^2$ are each independently $C_{1-10}$alkyl;
$R^3$ is —H, $C_{1-10}$alkyl, or $C_{0-6}$alkyl-COOR$^6$;
$R^{3'}$ is H, amino, cyano, halogen, aryl, aralkyl, heteroaryl, heteroaralkyl, carboxyl, $C_{1-10}$alkyl, $C_{1-10}$alkenyl, or $C_{1-10}$alkynyl, preferably H;
$R^4$ is —OH, —H, —CH$_3$, amino, —OC(O)C$_{1-10}$aralkyl, —OC(O)C$_{1-10}$alkyl, —OC(O)aryl, or a glutamine substituent; or
$R^3$ and $R^4$ together with the carbon atoms to which they are attached form a substituted or unsubstituted aromatic ring
$R^5$ is —OH, cyano, $C_{1-10}$alkoxy, amino, O-aralkyl, —OC(O) $C_{1-10}$aralkyl, —OC(O)C$_{1-10}$alkyl, —OC(O)aryl, or a glycine substituent; and
$R^6$ is H or $C_{1-10}$alkyl.

Other objects, features, and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
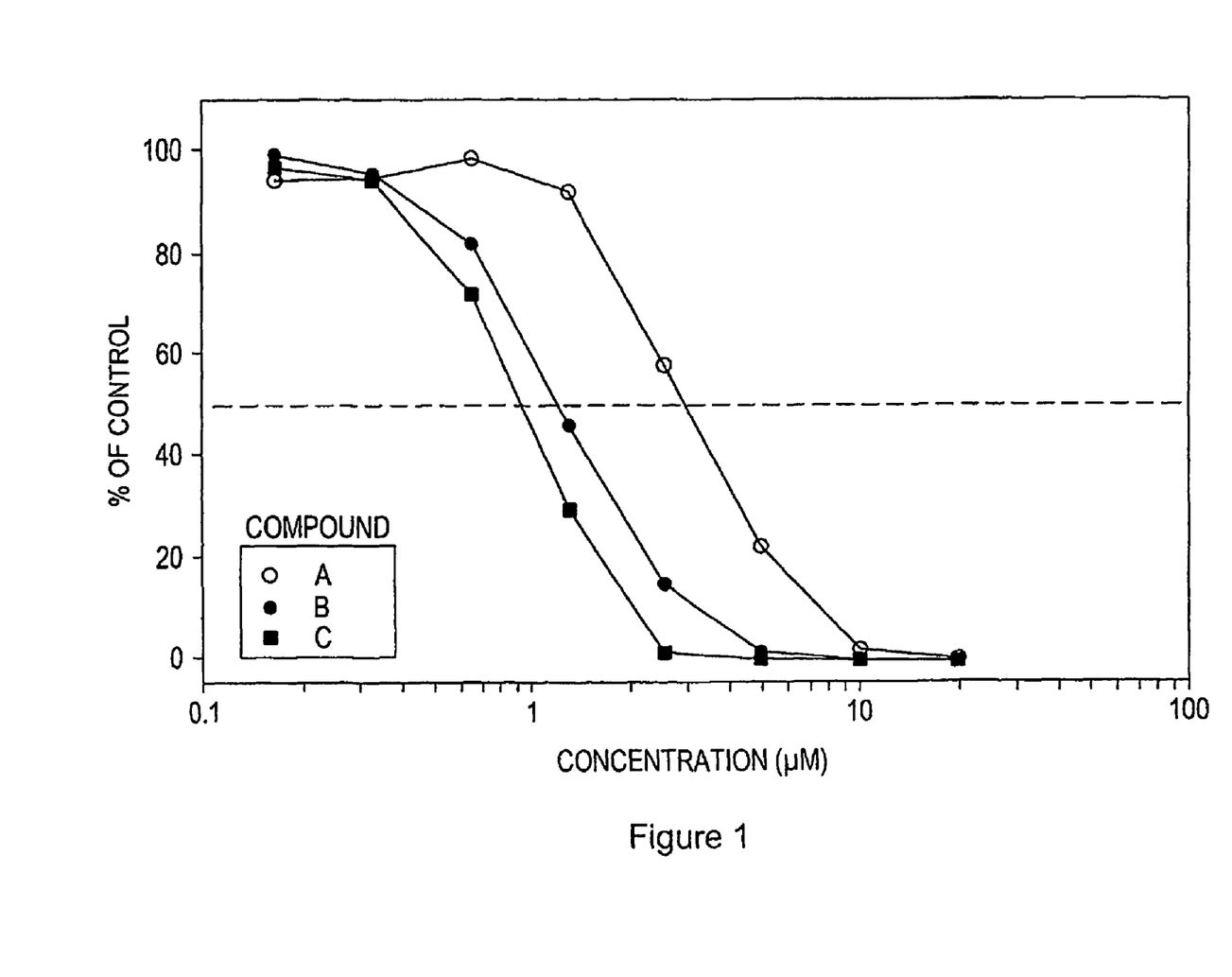
FIG. 1 shows the in vitro anti-proliferative response of HL-60 leukemia cells in the presence of arsenical compounds A, B, and C.
Figure 2:
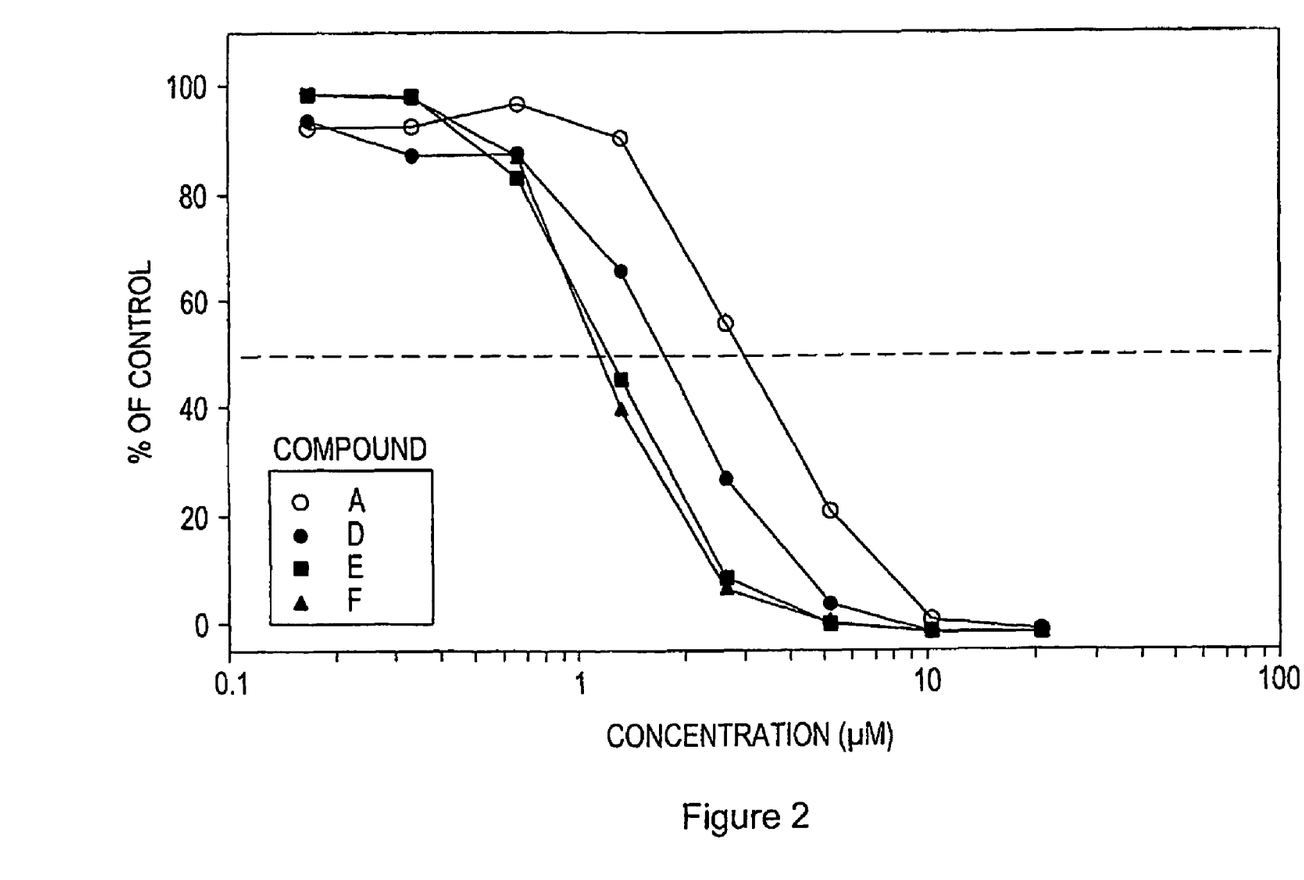
FIG. 2 shows the in vitro anti-proliferative response of HL-60 leukemia cells in the presence of arsenical compounds A, D, E, and F.

The present invention provides a number of organic arsenic compounds.

In certain embodiments, the organic arsenicals of the present invention have a structure of formula (I) or a pharmaceutically acceptable salt thereof (I)

wherein
X is S or Se, preferably S;
W is O, S, or (R)(R), where each occurrence of R is independently H or a $C_{1-2}$alkyl, preferably 0;
n is an integer from 2 to 20, preferably 9 to 14;
$R^1$ and $R^2$ are independently $C_{1-10}$alkyl, preferably $R^1$ and $R^2$ are independently selected from methyl, ethyl, propyl, and isopropyl;
$R^3$ is —H, $C_{1-10}$alkyl, or $C_{0-6}$alkyl-COOR$^6$, preferably H;
$R^{3'}$ is H, amino, cyano, halogen, aryl, aralkyl, heteroaryl, heteroaralkyl, carboxyl, $C_{1-10}$alkyl, $C_{1-10}$alkenyl, or $C_{1-10}$alkynyl, preferably H;
$R^4$ is —OH, —H, —CH$_3$, amino, —OC(O)C$_{1-10}$aralkyl, —OC(O)C$_{1-10}$alkyl, or —OC(O)aryl, preferably H;

$R^5$ is —OH, cyano, $C_{1-10}$alkoxy, amino, O-aralkyl, —OC(O)$C_{1-10}$aralkyl, —OC(O)$C_{1-10}$alkyl, or —OC(O)aryl, preferably OH or $C_{1-10}$alkoxy, more preferably OH; and $R^6$ is H or $C_{1-10}$alkyl, preferably H.

In certain embodiments, X is S, W is selected from 0 and (H)(H), preferably O, and n is an integer from 9 to 20. In certain such embodiments, n is an integer from 9 to 15.

In certain embodiments, $R^1$ and $R^2$ are independently selected from methyl, ethyl, propyl, and isopropyl. In certain embodiments, $R^1$ and $R^2$ are both methyl. In certain embodiments, $R^3$ and $R^{3'}$ are both H, $R^4$ is H, and $R^5$ is OH.

In certain embodiments, compounds of formula (I) are selected from

Another aspect of the invention relates to a method for the synthesis of a compound of formula (II)

wherein

X is S or Se, preferably S;

W is O, S, or (R)(R), where each occurrence of R is independently H or a $C_{1-2}$alkyl, preferably O or (R)(R);

n is 0 or 1, preferably 1;

$R^1$ and $R^2$ are independently $C_{1-10}$alkyl, preferably $R^1$ and $R^2$ are independently selected from methyl, ethyl, propyl, and isopropyl;

$R^3$ is —H or $C_{0-6}$alkyl-COOR$^6$;

$R^{3'}$ is H, amino, cyano, halogen, aryl, aralkyl, heteroaryl, heteroaralkyl, carboxyl, $C_{1-10}$alkyl, $C_{1-10}$alkenyl, or $C_{1-10}$alkynyl, preferably H;

$R^4$ is —OH, —H, —CH$_3$, —OC(O)$C_{1-10}$aralkyl, —OC(O)$C_{1-10}$alkyl, —OC(O)aryl, or a glutamine;

$R^5$ is —OH, cyano, $C_{1-10}$alkoxy, amino, O-aralkyl, —OC(O)$C_{1-10}$aralkyl, —OC(O)$C_{1-10}$alkyl, —OC(O)aryl, or a glycine substituent; and

$R^6$ is H or $C_{1-10}$alkyl, preferably H, wherein a compound having a structure of formula $(R^1)(R^2)AsCl$ is reacted with a compound having a structure of formula (III)

in the presence of an amine to provide a compound of formula (II).

Preferably the amine is selected such that the hydrochloride salt of the amine is soluble in methylene chloride. In certain embodiments, the amine is selected from trimethylamine, triethylamine, and triisopropylamine, preferably trimethylamine.

In certain embodiments, the reaction mixture is free of pyridine.

In certain preferred embodiments, a compound of formula $(R^1)(R^2)AsCl$ wherein $R^1$ and $R^2$ are independently $C_{1-10}$alkyl, preferably $R^1$ and $R^2$ are independently selected from methyl, ethyl, propyl, and isopropyl;

is reacted with a compound having a structure of formula in the presence of an amine to provide a compound of formula (II). In certain such embodiments, the amine is selected such that the hydrochloride salt of the amine is soluble in methylene chloride. In certain such embodiments the amine is selected from trimethylamine, triethylamine, and triisopropylamine, preferably trimethylamine.

In certain embodiments, a compound of formula (II) may be purified by washing (e.g., as a solution or a solid, such as crystals) with an organic solvent, preferably an organic solvent in which contaminants such as the hydrochloride salt of the amine as described above is soluble, preferably methylene chloride.

If a chiral center is present, all isomeric forms are within the scope of the invention. Regarding the stereochemistry, the Cahn-Ingold-Prelog rules for determining absolute stereochemistry are followed. These rules are described, for example, in *Organic Chemistry* Fox and Whitesell; Jones and Bartlett Publishers, Boston, Mass. (1994); Section 5-6, pp 177-178, which section is hereby incorporated by reference.

The invention further provides pharmaceutical compositions comprising a compound of formula (I) or (II), or a pharmaceutically acceptable salt thereof, and a pharmaceutically acceptable diluent or carrier. In certain embodiments, the pharmaceutical composition is an aqueous solution that has a pH greater than about 5, preferably in the range from about 5 to about 8, more preferably in the range from about 5 to about 7.

Another aspect of the invention provides a method for the treatment of cancer comprising administering a therapeutically effective amount of a compound of formula (I) or (II).

The invention also relates to the use of a compound of formula (I) or (II), or a pharmaceutically acceptable salt thereof, in the manufacture of a medicament for the treatment of cancer.

In certain embodiments, the cancer is selected from a solid tumor, such as brain, lung, liver, spleen, kidney (such as renal cell and renal pelvis), lymph node, small intestine, pancreas, blood cells, bone, colon/colorectal, stomach, breast, endometrium, prostate, testicle, ovary, central nervous system, skin, head and neck, esophagus, or bone marrow, or a hematological cancer, such as leukemia, acute promyelocytic leukemia, lymphoma, multiple myeloma, myelodysplasia, myeloproliferative disease, or refractory anemia. In certain embodiments, the cancer is a leukemia selected from acute and chronic leukemia.

Thus, in another aspect, the invention comprises a method of treating a patient with cancer comprising administering to the patient a composition comprising a compound of formula I, or pharmaceutical composition as described above. The therapeutically effective amount of a compound may be 0.1-1000 mg/kg, 1-500 mg/kg, or 10-100 mg/kg. In particular embodiments, the method may comprise administering the composition daily. It is further contemplated that treatment methods may involve multiple administrations. The method may comprise administering the compound daily such as by injection. Alternative routes and methods of administration described in the specification may also be used and the mode of administration will mainly depend on the type and location of the cancer. In certain embodiments, the method further comprises administering one or more additional agents to the patient. The additional agent may be all-trans-retinoic acid, 9-cis retinoic acid, Am-80, or ascorbic acid. The use of other adjunct cancer therapies, such as chemotherapy, radiotherapy, gene therapy, hormone therapy, and other cancer therapies known in the art are also contemplated in conjunction with the methods of the present invention.

Various methods of administration are contemplated, including regional, systemic, direct administration and by perfusion. Such methods include administration by injection, oral routes, intravenous, intrathecal, intraarterial, intratumoral, administration to tumoral vasculature, intraperitoneal, intratracheal, intramuscular, endoscopical, intralesional, percutaneous, subcutaneous, topical, nasal, buccal, mucosal, anogenital, rectal and the like.

DEFINITIONS

The term "$C_{x-y}$alkyl" refers to substituted or unsubstituted saturated hydrocarbon groups, including straight-chain alkyl and branched-chain alkyl groups that contain from x to y carbons in the chain, including haloalkyl groups such as trifluoromethyl and 2,2,2-trifluoroethyl, etc. $C_0$alkyl indicates a hydrogen where the group is in a terminal position, a bond if internal. The terms "$C_{2-y}$alkenyl" and "$C_{2-y}$alkynyl" refer to substituted or unsubstituted unsaturated aliphatic groups analogous in length and possible substitution to the alkyls described above, but that contain at least one double or triple bond respectively.

The term "$C_{1-6}$alkoxy" refers to an $C_{1-6}$alkyl group having an oxygen attached thereto. Representative alkoxy groups include methoxy, ethoxy, propoxy, tert-butoxy and the like. An "ether" is two hydrocarbons covalently linked by an oxygen. Accordingly, the substituent of an alkyl that renders that alkyl an ether is or resembles an alkoxy.

The term "$C_{1-6}$aralkyl", as used herein, refers to a $C_{1-6}$alkyl group substituted with an aryl group.

The term "aryl" as used herein includes 5-, 6-, and 7-membered substituted or unsubstituted single-ring aromatic groups in which each atom of the ring is carbon. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The phrase "pharmaceutically acceptable" is employed herein to refer to those ligands, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The term "preventing" is art-recognized, and when used in relation to a condition, such as a local recurrence (e.g., pain), a disease such as cancer, a syndrome complex such as heart failure or any other medical condition, is well understood in the art, and includes administration of a composition which reduces the frequency of, or delays the onset of, symptoms of a medical condition in a subject relative to a subject which does not receive the composition. Thus, prevention of cancer includes, for example, reducing the number of detectable cancerous growths in a population of patients receiving a prophylactic treatment relative to an untreated control population, and/or delaying the appearance of detectable cancerous growths in a treated population versus an untreated control population, e.g., by a statistically and/or clinically significant amount. Prevention of an infection includes, for example, reducing the number of diagnoses of the infection in a treated population versus an untreated control population, and/or delaying the onset of symptoms of the infection in a treated population versus an untreated control population. Prevention of pain includes, for example, reducing the magnitude of, or alternatively delaying, pain sensations experienced by subjects in a treated population versus an untreated control population.

The term "prophylactic or therapeutic" treatment is art-recognized and includes administration to the host of one or more of the subject compositions. If it is administered prior to clinical manifestation of the unwanted condition (e.g., disease or other unwanted state of the host animal) then the treatment is prophylactic, (i.e., it protects the host against developing the unwanted condition), whereas if it is administered after manifestation of the unwanted condition, the treatment is therapeutic, (i.e., it is intended to diminish, ameliorate, or stabilize the existing unwanted condition or side effects thereof).

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

A "therapeutically effective amount" of a compound with respect to the subject method of treatment refers to an amount of the compound(s) in a preparation which, when administered as part of a desired dosage regimen (to a mammal, preferably a human) alleviates a symptom, ameliorates a condition, or slows the onset of disease conditions according to clinically acceptable standards for the disorder or condition to be treated or the cosmetic purpose, e.g., at a reasonable benefit/risk ratio applicable to any medical treatment.

As used herein, the term "treating" or "treatment" includes reversing, reducing, or arresting the symptoms, clinical signs, and underlying pathology of a condition in manner to improve or stabilize a subject's condition.

Toxicity of Inorganic Vs. Organic Arsenicals

The use of arsenic trioxide is limited by its toxicity. OA, on the other hand, are much less toxic, to the extent that the methylation of inorganic arsenic in vivo into OA has been considered to be a detoxification reaction. The OA monomethylarsinic acid and dimethylarsinic acid are the primary metabolites of inorganic arsenic (Hughes et al., 1998). Inorganic arsenicals, including arsenic trioxide, have varied effects on many organ systems, including cardiovascular system, gastrointestinal tract, kidneys, skin, nervous system, and blood. Inorganic arsenicals are particularly toxic to the liver, causing infiltration, central necrosis, and cirrhosis (IARC, 1980: ACGIH, 1991; Beliles et al., 1994; Goyer et al., 1996). There is now sufficient evidence that inorganic arsenic compounds are skin and lung carcinogens in humans (Goyer et al., 1996).

The toxicity of a given arsenical is related to the rate of its clearance from the body and to the extent of its tissue accumulation (Beliles et al., 1994). In general, toxicity increases in the following sequence: organic arsenicals$<As^{5+}<As^{3+}$ (including arsenic trioxide)$<$arsine. Unlike inorganic arsenicals, no deaths or serious cases of toxicity due to OA have been reported in the literature. Consequently, in mammals the methylation of inorganic arsenic has been considered a detoxification mechanism because of the lower toxicity of methylated OA, and their fast excretion and low retention (Beliles et al., 1994; Goyer et al., 1996). A good example is that of dimethylarsinic acid, an organic compound, the predominant urinary metabolite excreted by most mammals after exposure to inorganic arsenic, including arsenic trioxide. In in vivo toxicity studies in mice, after intraperitoneal administration of arsenic trioxide, the $LD_{50}$ (a dose at which 50% of animals die due to acute toxicity) was 10 mg/kg, (Investigator's Brochure, 1998), while after administration of dimethylarsinic acid, the $LD_{50}$ was 500 mg/kg (MSDS, 1998).

Cancer Treatment

The organic arsenicals of the current invention may be used to treat a variety of cancers, including all solid tumors and all hematological cancers, including leukemia, lymphoma, multiple myeloma, myelodysplasia, or myeloproliferative disorders. The organic arsenical can also be used to treat hematological cancers that have become refractory to other forms of treatment.

Leukemia is a malignant neoplasm of blood-forming tissues, characterized by abnormal proliferation of leukocytes and is one of the four major types of cancer. Leukemias are classified according to the type of leucocyte most prominently involved. Acute leukemias are predominantly undifferentiated cell populations and chronic leukemias have more mature cell forms (WO9924029).

The acute leukemias are divided into lymphoblastic (ALL) and non-lymphoblastic (ANLL) types and may be further subdivided by morphologic and cytochemical appearance according to the French-American-British classification or according to their type and degree of differentiation. Specific B- and T-cell, as well as myeloid cell surface markers/antigens are used in the classification too. ALL is predominantly a childhood disease while ANLL, also known as acute myeloid leukemia, is a more common acute leukemia among adults.

Chronic leukemias are divided into lymphocytic (CLL) and myeloid (CML) types. CLL is characterized by the increased number of mature lymphocytes in blood, bone marrow, and lymphoid organs. Most CLL patients have clonal expansion of lymphocytes with B cell characteristics. CLL is a disease of older persons. In CML, the granulocytic cells predominate at all stages of differentiation in blood and bone marrow, but may also affect liver, spleen, and other organs. Other malignant hematological disease that may be treated with the OA of the current invention, include, but are not limited to: myelodysplasia, myeloproliferative diseases, lymphomas, and multiple myeloma.

Pharmaceutical Compositions

The preparation of a pharmaceutical composition that contains at least one organic arsenical or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329, incorporated herein by reference). Except insofar as any conventional carrier is incompatible with the active ingredient, its use in the therapeutic or pharmaceutical compositions is contemplated.

The organic arsenical may be combined with different types of carriers depending on whether it is to be administered in solid, liquid or aerosol form, and whether it need to be sterile for such routes of administration as injection. The present invention can be administered intravenously, intrathecally, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, injection, infusion, continuous infusion, localized perfusion bathing target cells directly, via a catheter, via a lavage, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The actual dosage amount of a composition of the present invention administered to a patient can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an organic arsenical compound. In other embodiments, the an active compound may comprise between about 2% to about 75% of the weight of the unit, or between about 25% to about 60%, for example, and any range derivable therein. In other non-limiting examples, a dose may also comprise from about 0.1 mg/kg/body weight, 0.5 mg/kg/body weight, 1 mg/kg/body weight, about 5 mg/kg/body weight, about 10 mg/kg/body weight, about 20 mg/kg/body weight, about 30 mg/kg/body weight, about 40 mg/kg/body weight, about 50 mg/kg/body weight, about 75 mg/kg/body weight, about 100 mg/kg/body weight, about 200 mg/kg/body weight, about 350 mg/kg/body weight, about 500 mg/kg/body weight, about 750 mg/kg/body weight, to about 1000 mg/kg/body weight or more per administration, and any range derivable therein. In non-limiting examples of a derivable range from the numbers listed herein, a range of about 10 mg/kg/body weight to about 100 mg/kg/body weight, etc., can be administered, based on the numbers described above.

In any case, the composition may comprise various antioxidants to retard oxidation of one or more component. Additionally, the prevention of the action of microorganisms can be brought about by preservatives such as various antibacterial and antifungal agents, including, but not limited to parabens (e.g., methylparabens, propylparabens), chlorobutanol, phenol, sorbic acid, thimerosal or combinations thereof.

The organic arsenical may be formulated into a composition in a free base, neutral or salt form. Pharmaceutically acceptable salts include the salts formed with the free carboxyl groups derived from inorganic bases such as for example, sodium, potassium, ammonium, calcium or ferric hydroxides; or such organic bases as isopropylamine, trimethylamine, histidine or procaine.

In embodiments where the composition is in a liquid form, a carrier can be a solvent or dispersion medium comprising, but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. In many cases, it will be preferable to include isotonic agents, such as, for example, sugars, sodium chloride or combinations thereof.

Sterile injectable solutions are prepared by incorporating the active compounds in the required amount of the appropriate solvent with various of the other ingredients enumerated above, as required, followed by filtered sterilization. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The preparation of highly concentrated compositions for direct injection is also contemplated, where the use of DMSO as solvent is envisioned to result in extremely rapid penetration, delivering high concentrations of the active agents to a small area.

The composition must be stable under the conditions of manufacture and storage, and preserved against the contaminating action of microorganisms, such as bacteria and fungi. Thus, preferred compositions have a pH greater than about 5, preferably from about 5 to about 8, more preferably from about 5 to about 7. It will be appreciated that endotoxin contamination should be kept minimally at a safe level, for example, less that 0.5 ng/mg protein.

In particular embodiments, prolonged absorption of an injectable composition can be brought about by the use in the compositions of agents delaying absorption, such as, for example, aluminum monostearate, gelatin or combinations thereof.

Combination Therapy

It is an aspect of this invention that the organic arsenical can be used in combination with another agent or therapy method, preferably another cancer treatment. The organic arsenical may precede or follow the other agent treatment by intervals ranging from minutes to weeks. In embodiments where the other agent and expression construct are applied separately to the cell, one would generally ensure that a significant period of time did not elapse between the time of each delivery, such that the agent and expression construct would still be able to exert an advantageously combined effect on the cell. For example, in such instances, it is contemplated that one may contact the cell, tissue or organism with two, three, four or more modalities substantially simultaneously (i.e., within less than about a minute) with the organic arsenical. In other aspects, one or more agents may be administered within about 1 minute, about 5 minutes, about 10 minutes, about 20 minutes about 30 minutes, about 45 minutes, about 60 minutes, about 2 hours, about 3 hours, about 4 hours, about 5 hours, about 6 hours, about 7 hours about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, about 24 hours, about 25 hours, about 26 hours, about 27 hours, about 28 hours, about 29 hours, about 30 hours, about 31 hours, about 32 hours, about 33 hours, about 34 hours, about 35 hours, about 36 hours, about 37 hours, about 38 hours, about 39 hours, about 40 hours, about 41 hours, about 42 hours, about 43 hours, about 44 hours, about 45 hours, about 46 hours, about 47 hours, to about 48 hours or more prior to and/or after administering the organic arsenical. In certain other embodiments, an agent may be administered within of from about 1 day, about 2 days, about 3 days, about 4 days, about 5 days, about 6 days, about 7 days, about 8 days, about 9 days, about 10 days, about 11 days, about 12 days, about 13 days, about 14 days, about 15 days, about 16 days, about 17 days, about 18 days, about 19 days, about 20, to about 21 days prior to and/or after administering the organic arsenical. In some situations, it may be desirable to extend the time period for treatment significantly, however, where several weeks (e.g., about 1, about 2, about 3, about 4, about 5, about 6, about 7 or about 8 weeks or more) lapse between the respective administrations.

Various combinations may be employed, the organic arsenical is "A" and the secondary agent, which can be any other therapeutic agent, is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

Administration of the therapeutic compositions of the present invention to a patient will follow general protocols for the administration of chemotherapeutics, taking into account the toxicity, if any. It is expected that the treatment cycles would be repeated as necessary. It also is contemplated that various standard therapies or adjunct cancer therapies, as well as surgical intervention, may be applied in combination with the described arsenical agent. These therapies include but are not limited to chemotherapy, radiotherapy, immunotherapy, gene therapy and surgery. The section below describes some adjunct cancer therapies:

Chemotherapy

Cancer therapies also include a variety of combination therapies with both chemical and radiation based treatments. Combination chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabien, navelbine, farnesyl-protein transferase inhibitors, transplatinum, 5-fluorouracil, vincristin, vinblastin and methotrexate, or any analog or derivative variant of the foregoing.

Radiotherapy

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells. The terms "contacted" and "exposed," when applied to a cell, are used herein to describe the process by which a therapeutic construct and a chemotherapeutic or radiotherapeutic agent are delivered to a target cell or are placed in direct juxtaposition with the target cell. To achieve cell killing or stasis, both agents are delivered to a cell in a combined amount effective to kill the cell or prevent it from dividing.

Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionucleotide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

Gene Therapy

In yet another embodiment, the secondary treatment is a secondary gene therapy in which a therapeutic polynucleotide is administered before, after, or at the same time a first therapeutic agent. Delivery of the therapeutic agent in conjunction with a vector encoding a gene product will have a combined anti-hyperproliferative effect on target tissues.

Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art will, in light of the present disclosure, appreciate that many changes can be made in the specific embodiments which are disclosed and still obtain a like or similar result without departing from the spirit and scope of the invention.

Example 1

Synthesis of 16-(dimethylarsino)thiohexadecanoic acid

A solution of 16-mercaptohexadecanoic acid (0.002 mol, 0.576 g) in dichloromethane (50 mL) was treated dropwise with dimethylchloroarsine (0.0033 mol, 0.046 g) followed by dropwise addition of triethylamine (0.4 g). The mixture was stirred and refluxed for at least four hours at which time the mixture was washed twice with water and dried over sodium sulfate. The solvent was removed under reduced pressure and the remaining residue was purified by column chromatography eluting with ethyl acetate and petroleum ether (1:10 v/v)

to produce the desired product ($IC_{10}<1$ μM, $IC_{50}<1.5$ μM, $IC_{90}<2.5$ μM, % Inhibition of DOX (1 μM)=100%).

Example 2

Synthesis of 11-(dimethylarsino)thioundecanoic acid 11-(Dimethylarsino)thioundecanoic acid was made using the procedure described above for the synthesis of 16-(dimethylarsino)thiohexadecanoic acid ($IC_{10}<1$ μM, $IC_{50}<1.5$ μM, $IC_{90}<2.5$ μM, % Inhibition of DOX (1 μM)=100%).

Example 3

Biological Assay

Cells

The HL-60 cell line was obtained from American Type Culture Collection (ATCC; Rockville Md.) and was grown in a 5% $CO_2$ humidified incubator at 37° C. in Iscove's Modified Dulbecco's Medium (IMDM; ATCC) supplemented with 20% fetal bovine serum (FBS; Atlanta Biologicals, Lawrenceville, Ga.) and 2 mM L-glutamine (Mediatech, Herndon, Va.), or "complete medium".

Test Compounds

All compounds (A-F) were received as lyophilized powders from IriSys, Inc. (San Diego, Calif.). They were solubilized in DMSO at 10 mM and diluted in complete medium and further diluted in IMDM containing DMSO such that the final DMSO concentration was 0.2% in all cultures. The known cytotoxic compound doxorubicin (Sigma Chemical Co., St. Louis, Mo.) was used as a positive control.

Compound A

Compound B

Compound C

Compound D

Compound E

Compound F

Cytotoxicity Assay

Flat bottom 96-well microtiter tissue culture plates (Costar, Cambridge, Mass.) were used for the assay. Cultures were performed in replicates of 8 wells; each well contained $1\times10^4$ cells. A day after plating the cells, wells were dosed with medium or test compounds. The final volume in each well was 200 μL. Each compound was tested on one plate; doxorubicin was used as a positive control on each plate. Wells contained either complete medium only (no cells; background), or cells plus medium (100% of control), 1 μM to 78.1 nM (performed as 2-fold dilutions). Plates were placed in a humidified 5% $CO_2$ incubator at 37° C. for three days. Proliferation was measured by the uptake of tritiated thymidine (3H-TdR) by pulsing wells with 1 μCi of $^3$H-TdR for the final 18 hours of incubation, harvesting the plate on a Brandel 96-well cell harvester (Gaithersburg, Md.) and measuring radioactivity on the filter mates in a Wallac 1450 Microbeta TriLux scintillation counter (Turku, Finland). The effects of the test compounds were determined by comparing the results of cells treated with test compounds with control cells (cells treated with complete medium only; 100% of control).

EQUIVALENTS

Those skilled in the art will recognize, or be able to ascertain using no more than routine experimentation, numerous equivalents to the compounds and methods of use thereof described herein. Such equivalents are considered to be within the scope of this invention and are covered by the following claims. Those skilled in the art will also recognize that all combinations of embodiments described herein are within the scope of the invention. All of the above-cited references and publications are hereby incorporated by reference.

The invention claimed is:

1. A compound having a structure of formula (I) or a pharmaceutically acceptable salt thereof (I)

wherein

X is S or Se;

W is O, S, or (R)(R), where each occurrence of R is independently H or a $C_{1-2}$alkyl;

n is an integer from 9 to 20;

$R^1$ and $R^2$ are independently $C_{1-10}$alkyl;

$R^3$ is —H, $C_{1-10}$alkyl, or $C_{0-6}$alkyl-$COOR^6$;

$R^{3'}$ is H, amino, cyano, halogen, aryl, aralkyl, heteroaryl, heteroaralkyl, carboxyl, $C_{1-10}$alkyl, $C_{1-10}$alkenyl, or $C_{1-10}$alkynyl;

R⁴ is —OH, —H, —CH₃, amino, —OC(O)C$_{1-10}$aralkyl, —OC(O)C$_{1-10}$alkyl, —OC(O)aryl, or a glutamine substituent;

R⁵ is —OH, cyano, C$_{1-10}$alkoxy, amino, O-aralkyl, —OC(O)C$_{1-10}$aralkyl, —OC(O)C$_{1-10}$alkyl, —OC(O)aryl, or a glycine substituent; and R⁶ is H or C$_{1-10}$alkyl.

2. A compound of claim 1, wherein W is O.

3. A compound of claim 1, wherein R⁵ is selected from OH and C$_{1-6}$alkoxy.

4. A compound of claim 1, wherein X is S.

5. A compound of claim 4, wherein R¹ and R² are the same and are together selected from methyl, ethyl, propyl, and isopropyl.

6. A compound of claim 5, wherein R³ and R³' are both H.

7. A compound of claim 6, wherein R⁴ is H.

8. A compound of claim 7, wherein n is an integer from 9 to 15.

9. A compound of claim 1, selected from

10. A pharmaceutical composition, comprising a compound of claim 1 and a pharmaceutically acceptable carrier or diluent.

11. The compound of claim 1, wherein R⁶ is H.

* * * * *